United States Patent [19]

Everly et al.

[11] 4,456,771

[45] Jun. 26, 1984

[54] CHEMICAL PROCESS FOR PREPARING 1,3-DIKETONES

[75] Inventors: Charles R. Everly; Jerry M. Roper, both of Baton Rouge, La.

[73] Assignee: Ethyl Corporation, Richmond, Va.

[21] Appl. No.: 415,020

[22] Filed: Sep. 7, 1982

[51] Int. Cl.$^3$ ............................................. C07C 45/61
[52] U.S. Cl. ................................... 568/315; 568/308; 568/325; 568/329; 44/77; 252/52 R; 252/404
[58] Field of Search .......................... 568/312, 315, 313

[56] References Cited

U.S. PATENT DOCUMENTS

| | | | |
|---|---|---|---|
| 4,060,556 | 11/1977 | Parker | 568/315 |
| 4,186,151 | 1/1980 | Kubota et al. | 568/315 |
| 4,208,425 | 6/1980 | Diana | 568/315 |

*Primary Examiner*—James H. Reamer
*Attorney, Agent, or Firm*—Donald L. Johnson; John F. Sieberth; Willard G. Montgomery

[57] ABSTRACT

Novel (3′,5′-dihydrocarbyl-4′-hydroxybenzyl)-1,3-diketones are prepared by reacting an N,N-dihydrocarbyl-2,6-dihydrocarbyl-4-aminomethylphenol with a 1,3-diketone and an alkyl halide in the presence of an alkali or an alkaline earth metal hydride. The products are useful as antioxidants.

31 Claims, No Drawings

CHEMICAL PROCESS FOR PREPARING 1,3-DIKETONES

CROSS-REFERENCE TO RELATED APPLICATION

This application is related to our co-pending U.S. application, Ser. No. 415,019, entitled CHEMICAL PROCESS, filed contemporaneously herewith on Sept. 7, 1982, directed to the preparation of novel (3',5'-dihydrocarbyl-4'-hydroxybenzyl)-1,3-diketones by reacting N,N-dihydrocarbyl-2,6-dihydrocarbyl-4-aminomethylphenol with a 1,3-diketone in the presence of a basic substance.

Technical Field

This invention relates to novel and eminently useful (3',5'-dihydrocarbyl-4'-hydroxybenzyl)-1,3-diketones and the preparation and uses thereof as antioxidants for oxidizable organic materials when such materials are exposed to oxidative degradative conditions.

The Invention

The materials of the invention are prepared by reacting an N,N-dihydrocarbyl-2,6-dihydrocarbyl-4-aminomethylphenol with a 1,3-diketone and an alkyl halide in the presence of an alkali or an alkaline earth metal hydride. Thus, in one embodiment of the invention there is provided a novel process for the preparation of (3',5'-dihydrocarbyl-4'-hydroxybenzyl)-1,3-diketones which comprises reacting an N,N-dihydrocarbyl-2,6-dihydrocarbyl-4-aminomethylphenol with a 1,3-diketone and an alkyl halide in the presence of an alkali or an alkaline earth metal hydride.

The process can be illustrated schematically by the following equations. Compounds having the general formula

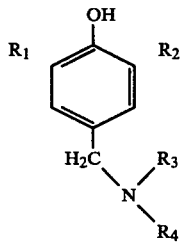

(I)

are reacted with compounds having the general formula

  (II)

and an alkyl halide of the general formula

  (III)

in the presence of an alkali or an alkaline earth metal hydride to yield a benzylated 1,3-diketone having the structural formula

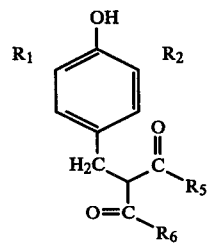

(IV)

In the structural formulas above $R_1$ and $R_2$ are the same or different and are hydrogen or hydrocarbyl radicals, preferably alkyl, aralkyl or cycloalkyl radicals having up to at least 40 carbon atoms, and preferably from 3 to 8 atoms, at least one of which is branched on the alpha-carbon atom, with the provision that at least one of $R_1$ or $R_2$ must be other than hydrogen; $R_3$ and $R_4$ are the same or different and are linear, branched or unbranched, alkyl, arallkyl or cycloalkyl radicals having up to at least 20 carbon atoms; $R_5$ and $R_6$ are the same or different and can be linear or branched alkyl radicals having up to at least 20 carbon atoms; $R_7$ is a linear or branched monovalent alkyl radical having up to at least 20 carbon atoms and X is bromine, chlorine or iodine.

Thus, in another embodiment of the present invention there is provided a process for the preparation of (3',5'-dihydrocarbyl-4'-hydroxybenzyl)-1,3-diketones having the general formula

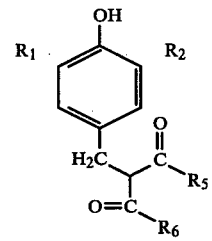

(IV)

which comprises reacting an N,N-dihydrocarbyl-2,6-dihydrocarbyl-4-aminomethylphenol of the general formula

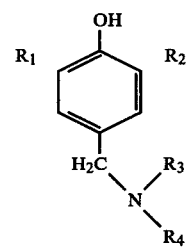

(I)

with a 1,3-diketone of the general formula

  (II)

and an alkyl halide of the formula

  (III)

in the presence of an alkali or an alkaline earth metal hydride wherein in the structural formulas above $R_1$ and $R_2$ are the same or different and are hydrogen or hydrocarbyl radicals having up to at least 40 carbon atoms with the provision that at least one of $R_1$ or $R_2$ must be other than hydrogen; $R_3$ and $R_4$ are the same or different and are linear, branched or unbranched alkyl, aralkyl or cycloalkyl radicals having up to at least 20 carbon atoms; $R_5$ and $R_6$ are the same or different and are linear or branched alkyl radicals having up to at least 20 carbon atoms; $R_7$ is a linear or branched monovalent alkyl radical having up to at least 20 carbon atoms and X is chlorine, bromine or iodine.

Representative examples of radicals described above are secondary radicals such as secondary butyl, secondary amyl, secondary octyl; tertiary radicals such as tertiary butyl, tertiary hexyl and tertiary decyl; alkyl radicals such as methyl, ethyl, propyl, butyl, nonyl, decyl, tetradecyl, hexadecyl, nonadecyl; aralkyl radicals such as methyl phenyl and pentyl phenyl, and cycloalkyl radicals such as cyclopentyl, cyclohexyl and cycloheptyl radicals.

Representative examples of the Group I compounds are
  N,N-dimethyl,2,6-di-t-butyl-4-aminomethylphenol,
  N,N-dimethyl,2-methyl-6-isopropyl-4-aminomethylphenol,
  N,N-dimethyl,2-methyl-6-t-butyl-4-aminomethylphenol,
  N,N-dimethyl,2,6-diisopropyl-4-aminomethylphenol,
  N,N-dimethyl,2-sec-butyl-4-aminomethylphenol,
  N,N-dimethyl,2-isopropyl-4-aminomethylphenol,
  N,N-dimethyl,2-t-butyl-4-aminomethylphenol,
  N,N-diethyl,2,6-di-t-butyl-4-aminomethylphenol,
  N,N-dioctyl,2,6-di-t-butyl-4-aminomethylphenol,
  N,N-dioctyl,2-ethyl-6-t-butyl-4-aminomethylphenol,
  N,N-dioctyl,2,6-diheptyl-4-aminomethylphenol,
  N,N-dioctyl,2-ethyl-6-methyl-4-aminomethylphenol,
  N,N-dioctyl,2-t-butyl-6-heptyl-4-aminomethylphenol,
  N-ethyl,N-methyl,2,6-di-t-butyl-4-aminomethylphenol,
  N-octyl,N-methyl,2-methyl-6-ethyl-4-aminomethylphenol,
  3,5-di-t-butyl-4-hydroxybenzylpiperidine,
  3,5-di-t-butyl-4-hydroxybenzylmorpholine, and
  3,5-di-t-butyl-4-hydroxybenzylpyrrolidine.

Representative examples of Group II 1,3-dicarbonyl compounds are
  2,4-pentanedione,
  2,4-heptanedione,
  4,6-nonanedione,
  2,6-dimethyl-3,5-heptanedione,
  1-hexyl-1,3-butanedione,
  1-hexyl-2,4-pentanedione, and
  1,3-dihexyl-1,3-propanedione.

Representative examples of Group III compounds are
  methyl iodide,
  octyl iodide,
  methyl bromide,
  octyl bromide,
  methyl chloride,
  octyl chloride,
  isopropyl iodide,
  isopropyl bromide,
  sec-butyliodide,
  sec-butylbromide, and
  3-methyliodobutane.

Representative examples of Group IV benzylated 1,3-diketone compounds, functioning as antioxidants, are
  3-(3',5'-di-t-butyl-4'-hydroxybenzyl)-2,4-pentanedione,
  3-(3'-methyl-5'-isopropyl-4'-hydroxybenzyl)-2,4-pentanedione,
  3-(3'-methyl-5'-t-butyl-4'-hydroxybenzyl)-2,4-pentanedione,
  3-(3',5'-diisopropyl-4'-hydroxybenzyl)-2,4-pentanedione,
  3-(3'-sec-butyl-4'-hydroxybenzyl)-2,4-pentanedione,
  3-(3'-isopropyl-4'-hydroxybenzyl)-2,4-pentanedione,
  3-(3'-t-butyl-4'-hydroxybenzyl)-2,4-pentanedione,
  3-(3'-ethyl-5'-methyl-4'-hydroxybenzyl)-2,4-heptanedione,
  5-(3',5'-dioctyl-4'-hydroxybenzyl)-4,6-nonanedione,
  4-(3'-t-butyl-5'-heptyl-4'-hydroxybenzyl)-2,6-dimethyl-3,5-heptanedione,
  2-(3',5'-dioctyl-4'-hydroxybenzyl)-1-hexyl-1,3-butanedione,
  3-(3',5'-dioctyl-4'-hydroxybenzyl)-1-hexyl-2,4-pentanedione, and
  2-(3',5'-dioctyl-4'-hydroxybenzyl)-1,3-dihexyl-1,3-propanedione.

In general, any of the alkali or alkaline earth metal hydrides may be used in the practice of the present process. These include sodium hydride, potassium hydride, lithium hydride, magnesium hydride, calcium hydride, and the like. Sodium hydride is preferred.

The process of the invention is carried out by reacting the benzylamine starting material with at least 1 molar equivalent of β-diketone reactant and 1 molar equivalent of alkyl halide although an excess of either or both diketone and halide reactant can be used. A preferred range of β-diketone reactant to benzylamine reactant is from about 1 to 10 moles of β-diketone per mole of benzylamine. A preferred range of alkyl halide reactant to benzylamine reactant ranges from about 1 to 10 moles of halide per mole of benzylamine.

At least 1 mole of hydride per mole of benzylamine reactant should be used in the process of the invention, although an amount of hydride up to 50 moles of hydride per mole of benzylamine reactant can be used, if desired.

The reaction is advantageously conducted at a temperature of from about 50° C. to about 500° C. While lower temperatures can be used, the reaction rates are generally correspondingly lower. Temperatures above 500° C. can be used, but excessive decomposition of the reaction components can occur. Reflux temperature at atmospheric pressure is effective and preferred.

Typically, the reaction can be conducted at atmospheric pressure. However, higher pressures up to about 1000 psig may be used, if desired.

The use of a solvent for the reaction mixture is not generally required, especially if an excess of 1,3-dicarbonyl or alkyl halide reactant is used. However, if desired, a solvent which is inert under the reaction conditions, i.e., those solvents which do not enter into the reaction, may be added to the reaction vessel. Useful solvents comprise aprotic solvents which include ethers such as diethyl ether, dibutyl ether, 1-ethoxyhexane, tetrahydrofuran, 1,4-dioxane, 1,3-dioxolane, diglyme, 1,2-diethoxyethane, etc. Especially useful solvents are dipolar aprotic solvents such as dimethyl sulfoxide, N,N-dimethylformamide, N,N-dimethylacetamide, dimethyl sulfone, tetramethylene sulfone, N-methylpyrrolidinone, acetonitrile and like materials. Other solvents which are inert under the reaction conditions may be used: for example, low boiling hydrocarbons, halogenated hydrocarbons, examples of which are benzene, toluene, tetrachloroethane, the chlorinated benzenes, the chlorinated toluenes, etc.

The amount of solvent can be expressed as a volume ratio of solvent to benzylamine reactant. Suitable volume ratios of solvent to benzylamine reactant can be from about 0/1 to about 500/1 and preferably from about 1/1 to about 300/1.

The mode of addition in the process is not particularly critical. Accordingly, it is convenient to add the benzylamine reactant to a mixture of the other materials, add the 1,3-dicarbonyl compound to a mixture of the other materials, add the alkyl halide reactant to a mixture of the other materials, add the reactants to a mixture of the benzylamine and solvent, introduce all ingredients simultaneously into the reaction zone, or the like.

The process should be carried out for the time sufficient to convert substantially all of the benzylamine reactant to the corresponding benzylated 1,3-diketone. The length of time for optimum yield will depend primarily upon the reaction temperature and the particular solvent, if any, used in the reaction. In general, excellent yields of the benzylated 1,3-diketones are obtained in from about two to twenty-four hours.

Although not required, the process can be conducted in a substantially anhydrous reaction system, and accordingly, the components of the reaction system are brought together and maintained under a substantially dry, inert atmosphere. By "substantially anhydrous" is meant a reaction system wherein the total amount of water present is no more than about 5 percent by weight, based on the reaction mixture. When the amount of water in the system exceeds this, both reaction rate and yield of product decrease.

The process may readily be conducted in a batchwise, semibatch or continuous manner and in conventional equipment.

The process of the invention when run continuously can be illustrated schematically by the equation shown below. $R_1$, $R_2$, $R_3$, $R_4$, $R_5$, $R_6$ and $R_7$ are the same radicals and X represents the same halogens as described and exemplified above.

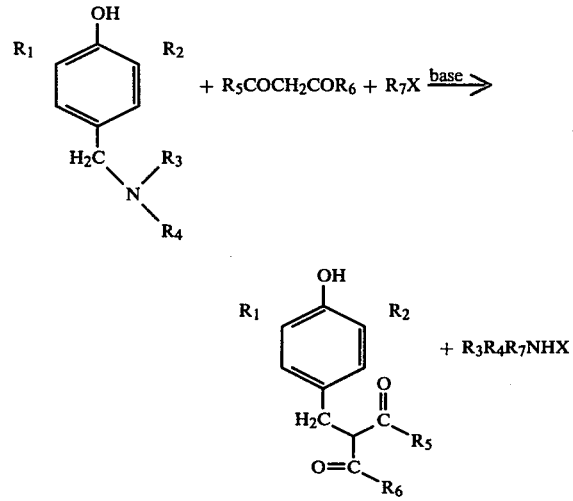

Under the reaction conditions, the benzylamine reactant is alkylated to initially yield a quaternary ammonium salt of the benzylamine which subsequently eliminates a tertiary amine component from the salt to produce a quinone methide intermediate which undergoes nucleophilic attack by the 1,3-diketone reactant to form the desired benzylated 1,3-diketone product. During the course of the reaction some bis(hydroxyphenyl)methane by-product may be formed.

The benzylated 1,3-diketone product is easily separated from the reaction mixture by such means as distillation, extraction, crystallization and other methods obvious to those skilled in the chemical processing art.

Since the benzylated 1,3-diketone products of the present process are believed to be novel compounds, in a still further embodiment of the present invention, there is provided, as new compositions of matter, compounds of the general formula

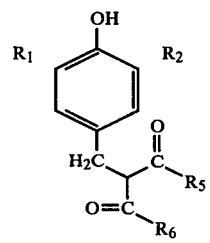

wherein $R_1$ and $R_2$ are the same or different and are hydrogen or hydrocarbyl radicals, preferably alkyl, aralkyl or cycloalkyl radicals, having up to at least 40 carbon atoms, and preferably from 3 to 8 carbon atoms, at least one of which is branched on the alpha-carbon atom, with the provision that at least one of $R_1$ or $R_2$ must be other than hydrogen and $R_5$ and $R_6$ are the same or different and are linear or branched alkyl radicals having up to at least 20 carbon atoms.

The benzylated 1,3-diketone products prepared by the process of this invention have antioxidant properties and are capable of stabilizing polymers normally subject to oxidative degradation when incorporated into the polymers using conventional techniques such as by addition to polymer lattices; or by addition to solid polymers on a mill or in a Banbury. Further, the novel compounds of this invention are effective antioxidants in both unleaded and leaded gasolines made from a wide variety of base stocks and for engine and industrial oils which are derived from crude petroleum or produced synthetically.

Thus, in another embodiment of the present invention there is provided a liquid hydrocarbon fuel of the gasoline boiling range for spark ignition internal combustion engines normally susceptible to deterioration in the presence of oxygen containing in an amount sufficient to inhibit such deterioration, a compound of the general formula

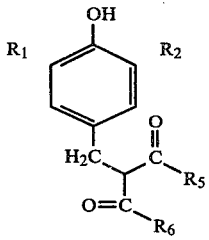

wherein $R_1$ and $R_2$ are the same or different and are hydrogen or hydrocarbyl radicals, preferably alkyl, aralkyl or cycloalkyl radicals, having up to at least 40 carbon atoms, and preferably from 3 to 8 carbon atoms, at least one of which is branched on the alpha-carbon atom, with the provision that at least one of $R_1$ or $R_2$ must be other than hydrogen and $R_5$ and $R_6$ are the same or different and are linear or branched alkyl radicals having up to at least 20 carbon atoms.

A still further embodiment of the present invention is lubricating oil normally susceptible to oxidative deterioration containing a small antioxidant quantity of a compound of the general formula

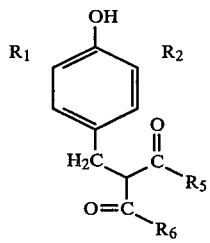

wherein $R_1$ and $R_2$ are the same or different and are hydrogen or hydrocarbyl radicals, preferably alkyl, aralkyl or cycloalkyl radicals, having up to at least 40 carbon atoms, and preferably from 3 to 8 carbon atoms, at least one of which is branched on the alpha-carbon atom, with the provision that at least one of $R_1$ or $R_2$ must be other than hydrogen and $R_5$ and $R_6$ are the same or different and are linear or branched alkyl radicals having up to at least 20 carbon atoms.

The practice of this invention will be still further apparent by the following illustrative examples.

EXAMPLE I

In a 250 mL glass reaction vessel, a tetrahydrofuran solution (55 mLs) of N,N-dimethyl,2,6-di-t-butyl-4-aminomethylphenol (1.32 g, 5 mmols) was treated with methyl iodide (5 mmols) under a nitrogen atmosphere to give a colorless slurry. In a separate vessel, a tetrahydrofuran solution (30 mLs) of acetylacetone (1.0 g, 10 mmols) was stirred with sodium hydride (0.24 g, 10 mmols) for 5 minutes under a nitrogen atmosphere. The resultant milky suspension was quickly added to the tetrahydrofuran slurry containing N,N-dimethyl,2,6-di-t-butyl-4-aminomethyl-phenol and methyl iodide. The reaction mixture was refluxed under nitrogen for 4 hours. After cooling, the reaction slurry was poured into cold 2N hydrochloric acid (50 mLs) which was then extracted with diethyl ether (2×20 mLs). The combined extracts were dried (MgSO$_4$) and concentrated in vacuo to afford a reddish black oil (1.73 g) which was shown by VPC to contain 3-(3',5'-di-t-butyl-4'-hydroxyphenyl)-2,4-pentanedione (80%), N,N-dimethyl,2,6-di-t-butyl-amino-methylphenol (8%).

EXAMPLE II

In a 250 mL glass reaction vessel, a dimethylformamide solution (20 mLs) of N,N-dimethyl,2,6-di-t-butyl-4-aminomethylphenol (2.63 g, 10 mmols) was treated with methyl iodide (10 mmols) under a nitrogen atmosphere to give a colorless slurry. In a separate vessel, a dimethylformamide solution (20 mmols) of acetylacetone (1.2 g, 12 mmols) was stirred with sodium hydride (0.34 g, 14 mmols) for 5 minutes under a nitrogen atmosphere. The resultant milky suspension was quickly added to the dimethylformamide suspension containing N,N-dimethyl,2,6-di-t-butyl-4-aminomethylphenol and methyl iodide. The reaction mixture was heated to 110° C. and maintained at that temperature for 24 hours. After cooling, the reaction slurry was poured into cold 2N hydrochloric acid (50 mLs) which was then extracted with diethyl ether (2×20 mLs). The combined extracts were dried (MgSO$_4$) and concentrated in vacuo to afford a black oil (2.11 g) which was shown by VPC to contain 3-(3',5'-di-t-butyl-4'-hydroxybenzyl)-2,4-pentanedione (52%).

EXAMPLE III

In a 250 mL glass reaction vessel, a tetrahydrofuran solution (100 mLs) of N,N-dimethyl,2,6-di-t-butyl-4-aminomethylphenol (10.5 g, 40 mmols) was treated with methyl iodide (40 mmols) under a nitrogen atmosphere to give a colorless slurry. In a separate vessel, a tetrahydrofuran solution (100 mLs) of acetylacetone (4.2 g, 42 mmols) was stirred with sodium hydride (1.0 g, 42 mmols) for 5 minutes under a nitrogen atmosphere. The resultant milky suspension was quickly added to the tetrahydrofuran slurry containing N,N-dimethyl,2,6-di-t-butyl-4-aminomethylphenol and methyl iodide. The reaction mixture was refluxed under nitrogen for 3.5 hours. After cooling, the reaction slurry was poured into cold 2N hydrochloric acid (50 mLs) which was then extracted with diethyl ether (2×20 mLs). The combined extracts were dried (MgSO$_4$) and concentrated in vacuo to afford a black oil (10.1 g) which was shown by VPC to contain 3-(3',5'-di-t-butyl-4'-hydroxyphenyl)-2,4-pentanedione (58%).

Having disclosed the process of the present invention, one skilled in the art can readily envision various modifications and changes which are nevertheless within the scope of the invention. Therefore, it is desired that the process of this invention be limited only by the lawful scope of the appended claims.

We claim:

1. A process for the preparation of a compound having the general structural formula

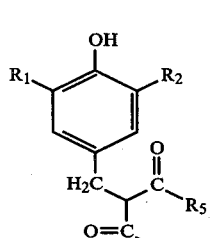 (IV)

which comprises reacting a compound of the general structural formula

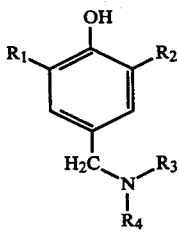

(I)

with a 1,3-diketone of the general structural formula $R_5COCH_2COR_6$ (II)

and an alkyl halide of the general formula $R_7X$ (III)

in the presence of an alkali metal hydride or an alkaline earth metal hydride wherein $R_1$ and $R_2$ are the same or different and are hydrogen or hydrocarbyl radicals having up to at least 40 carbon atoms with the provision that at least one of $R_1$ or $R_2$ must be other than hydrogen, $R_3$ and $R_4$ are the same or different and are linear, branched or unbranched alkyl, aralkyl or cycloalkyl radicals having up to at least 20 carbon atoms, or $R_3$ and $R_4$ taken together form a piperidine, morpholine, or pyrrolidine ring, $R_5$ and $R_6$ are the same or different and are linear or branched alkyl radicals having up to at least 20 carbon atoms; $R_7$ is a linear or branched monovalent alkyl radical having up to at least 20 carbon atoms and X is chlorine, bromine or iodine.

2. The process of claim 1 wherein compounds having the general structural formula (I) are selected from the group consisting of N,N-dimethyl,2,6-di-t-butyl-4-aminomethylphenol, N,N-dimethyl,2-methyl-6-isopropyl-4-aminomethyl-phenol, N,N-dimethyl,2-methyl-6-t-butyl-4-aminomethyl-phenol, N,N-dimethyl,2,6-diisopropyl-4-aminomethylphenol, N,N-dimethyl,2-sec-butyl-4-aminomethylphenol, N,N-dimethyl,2-isopropyl-4-aminomethylphenol, N,N-dimethyl,2-t-butyl-4-aminomethylphenol, N,N-diethyl,2,6-di-t-butyl-4-aminomethylphenol, N,N-dioctyl,2,6-di-t-butyl-4-aminomethylphenol, N,N-dioctyl,2-ethyl-6-t-butyl-4-aminomethylphenol, N,N-dioctyl,2,6-diheptyl-4-aminomethylphenol, N,N-dioctyl,2-ethyl-6-methyl-4-aminomethylphenol, N,N-di-octyl,2-t-butyl-6-heptyl-4-aminomethylphenol, N-ethyl,N-methyl,2,6-di-t-butyl-4-aminomethylphenol, N-octyl,N-methyl,2-methyl-6-ethyl-4-aminomethylphenol, 3,5-di-t-butyl-4-hydroxybenzylpiperidine, 3,5-di-t-butyl-4-hydroxybenzylmorpholine, and 3,5-di-t-butyl-4-hydroxybenzylpyrrolidine.

3. The process of claim 1 wherein compounds having the general structural formula (II) are selected from the group consisting of 2,4-pentanedione, 2,4-heptanedione, 4,6-nonanedione, 2,6-dimethyl-3,5-heptanedione, 1-hexyl-1,3-butanedione, 1-hexyl-2,4-pentanedione, and 1,3-dihexyl-1,3-propanedione.

4. The process of claim 1 wherein compounds having the general structural formula (III) are selected from the group consisting of methyl iodide, octyl iodide, methyl bromide, octyl bromide, methyl chloride, octyl chloride, isopropyl iodide, isopropyl bromide, sec-butyliodide, sec-butylbromide, and 3-methyliodobutane.

5. The process of claim 1 wherein said alkali metal hydride or alkaline earth metal hydride is selected from the group consisting of sodium hydride, barium hydride, lithium hydride, magnesium hydride and calcium hydride.

6. The process of claim 1 wherein the compound produced is 3-(3',5'-di-t-butyl-4'-hydroxybenzyl)-2,4-pentanedione.

7. The process of claim 1 wherein the compound produced is 3-(3'-methyl-5'-isopropyl-4'-hydroxybenzyl)-2,4-pentanedione.

8. The process of claim 1 wherein the compound produced is 3-(3'-methyl-5'-t-butyl-4'-hydroxybenzyl)-2,4-pentanedione.

9. The process of claim 1 wherein the compound produced is 3-(3',5'-diisopropyl-4'-hydroxybenzyl)-2,4-pentanedione.

10. The process of claim 1 wherein the compound produced is 3-(3'-sec-butyl-4-hydroxybenzyl)-2,4-pentandeione.

11. The process of claim 1 wherein the compound produced is 3'(3'-isopropyl-4'-hydroxybenzyl)-2,4-pentanedione.

12. The process of claim 1 wherein the compound produced is 3-(3'-t-butyl-4'-hydroxybenzyl)-2,4-pentanedione.

13. The process of claim 1 wherein the compound produced is 3-(3'-ethyl-5'-methyl-4'-hydroxybenzyl)-2,4-heptanedione.

14. The process of claim 1 wherein the compound produced is 5-(3',5'-dioctyl-4'-hydroxybenzyl)-4,6-nonanedione.

15. The process of claim 1 wherein the compound produced is 4-(3'-t-butyl-5'-heptyl-4'-hydroxybenzyl)-2,6-dimethyl-3,5-heptanedione.

16. The process of claim 1 wherein the compound produced is 2-(3',5'-dioctyl-4'-hydroxybenzyl)-1-hexyl-1,3-butanedione.

17. The process of claim 1 wherein the compound produced is 3-(3',5'-dioctyl-4'-hydroxybenzyl)-1-hexyl-2,4-pentanedione.

18. The process of claim 1 wherein the compound produced is 2-(3',5'-dioctyl-4'-hydroxybenzyl)-1,3-dihexyl-1,3-propanedione.

19. The process of claim 1 wherein the molar ratio of 1,3-diketone reaction to benzylamine reactant is from about 1-10 moles of diketone per mole of benzylamine.

20. The process of claim 1 wherein the molar ratio of alkyl halide reactant to benzylamine reactant is from about 1-10 moles of alkyl halide per mole of benzylamine.

21. The process of claim 1 wherein said reaction is conducted at elevated temperature.

22. The process of claim 21 wherein said reaction is carried out at a temperature of from about 50° C. to about 500° C.

23. The process of claim 1 wherein said reaction is carried out under pressure in the range of from about atmospheric up to about 1000 psig.

24. The process of claim 1 wherein said reaction is carried out at temperature in the range of about 50° C. to about 500° C. and under pressure in the range of about atmospheric to about 1000 psig.

25. The process of claim 1 wherein said reaction is carried out in the presence of a solvent which is inert under the reaction conditions.

26. The process of claim 25 wherein the said solvent is an aprotic solvent.

27. The process of claim 25 wherein said aprotic solvent is a dipolar aprotic solvent.

28. The process of claim 27 wherein said dipolar aprotic solvent is selected from dimethyl sulfoxide, N,N-dimethylformamide, N,N-dimethylacetamide, dimethyl sulfone, tetramethylene sulfone, N-methylpyrrolidinone and acetonitrile.

29. The process of claim 25 wherein said solvent is selected from the group consisting of low boiling hydrocarbons and halogenated hydrocarbons.

30. The process of claim 25 wherein the volume ratio of solvent to benzylamine reactant is from about 0/1 to about 500/1.

31. The process of claim 1 wherein the reaction is carried out under a substantially dry inert atmosphere.

* * * * *

UNITED STATES PATENT AND TRADEMARK OFFICE
CERTIFICATE OF CORRECTION

PATENT NO. : 4,456,771
DATED : June 26, 1984
INVENTOR(S) : Charles R. Everly et al.

It is certified that error appears in the above—identified patent and that said Letters Patent is hereby corrected as shown below:

Column 8, line 1,  " -4'-hydroxyphenyl)- " should read
      -- -4'-hydroxybenzyl)- --;
    lines 44-45, " -4'-hydroxyphenyl)- " should read
      -- -4'-hydroxybenzyl)- --;
Column 10, line 16, " 3-(3'-sec-butyl-4-hydroxy- " should read
      -- 3-(3'-sec-butyl-4'-hydroxy- --;
    line 44, " reaction " should read -- reactant --;
Column 12, line 4, " 0/1 " should read -- 1/1 --.

Signed and Sealed this

Twelfth Day of February 1985

[SEAL]

Attest:

DONALD J. QUIGG

Attesting Officer    Acting Commissioner of Patents and Trademarks